United States Patent
Nicholson et al.

(10) Patent No.: US 6,352,704 B1
(45) Date of Patent: Mar. 5, 2002

(54) FLAVORED CYANOACRYLATE COMPOSITIONS

(75) Inventors: William S. C. Nicholson; Upvan Narang, both of Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/343,914

(22) Filed: Jun. 30, 1999

(51) Int. Cl.$^7$ .......................... A01N 25/24; A61K 9/00; A61K 6/00; A61K 7/00; A61K 7/16; A61K 31/74; A61K 31/785; A61K 31/795

(52) U.S. Cl. .................. 424/407; 424/400; 424/401; 424/49; 424/78.31; 424/78.35

(58) Field of Search .................. 424/78.35, 78.31, 424/77, 401, 407, 49, 400; 206/524.1; 606/214

(56) References Cited

U.S. PATENT DOCUMENTS

| | | | |
|---|---|---|---|
| 2,721,858 A | 10/1955 | Joyner et al. | |
| 3,254,111 A | 5/1966 | Hawkins et al. | |
| 3,360,124 A | * 12/1967 | Stonehill | |
| 3,554,990 A | 1/1971 | Quinn et al. | |
| 3,940,362 A | 2/1976 | Overhults | |
| 3,966,902 A | 6/1976 | Chromecek | |
| 3,995,641 A | 12/1976 | Kronenthal et al. | |
| 4,127,382 A | 11/1978 | Perry | |
| 4,171,416 A | 10/1979 | Motegi et al. | |
| 4,313,865 A | 2/1982 | Teramoto et al. | |
| 4,321,180 A | 3/1982 | Kimura et al. | |
| 4,364,876 A | 12/1982 | Kimura et al. | |
| 4,560,723 A | 12/1985 | Millet et al. | |
| 4,582,648 A | 4/1986 | Hirakawa | |
| 4,720,513 A | * 1/1988 | Kameyama et al. | ........ 523/203 |
| 5,259,835 A | 11/1993 | Clark et al. | |
| 5,306,490 A | 4/1994 | Barley, Jr. | |
| 5,328,687 A | 7/1994 | Leung et al. | |
| 5,480,935 A | 1/1996 | Greff et al. | |
| 5,514,371 A | 5/1996 | Leung et al. | |
| 5,514,372 A | 5/1996 | Leung et al. | |
| 5,530,037 A | * 6/1996 | McDonnell et al. | .......... 522/79 |
| 5,554,365 A | 9/1996 | Byram et al. | |
| 5,575,997 A | 11/1996 | Leung et al. | |
| 5,582,834 A | 12/1996 | Leung et al. | |
| 5,624,669 A | 4/1997 | Leung et al. | |
| 5,665,817 A | 9/1997 | Greff et al. | |
| 5,730,994 A | 3/1998 | Askill et al. | |
| 5,760,102 A | * 6/1998 | Hall et al. | .................. 523/120 |
| 5,807,563 A | 9/1998 | Askill et al. | |

FOREIGN PATENT DOCUMENTS

| | | |
|---|---|---|
| JP | 51-133501 | 11/1976 |
| JP | 52-37535 | 3/1977 |
| JP | A-53-058541 | 5/1978 |
| JP | A-55-036415 | 3/1980 |
| JP | A-01-299217 | 12/1989 |

* cited by examiner

Primary Examiner—Dameron L. Jones
Assistant Examiner—Lauren Q Wells
(74) Attorney, Agent, or Firm—Oliff & Berridge, PLC

(57) ABSTRACT

A sterile or non-sterile flavored monomeric adhesive composition includes a flavoring additive and a monomer. The composition can be applied, for example, to skin or the inside of the mouth. A method of making a sterile, flavored adhesive composition includes placing a mixture of a polymerizable adhesive monomer and a flavoring additive in a container, sealing the container, and sterilizing the mixture and the container. The flavored adhesive composition is particularly useful as a medical adhesive and can include 1,1-disubstituted ethylene monomers, such as α-cyanoacrylates.

37 Claims, 1 Drawing Sheet

FLAVORED CYANOACRYLATE COMPOSITIONS

BACKGROUND OF THE INVENTION

1. Field of Invention

The invention relates to flavored monomer and polymer adhesive and sealant compositions, and to their production and use.

2. Description of Related Art

Monomer and polymer adhesives are used in both industrial (including household) and medical applications. Included among these adhesives are the 1, 1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate and an adjunct to surgical sutures and staples in wound closure as well as for covering and protecting surface wounds such as lacerations, abrasions, burns, stomatitis, sores, and other open surface wounds. When an adhesive is applied, it is usually applied in its monomeric form, and the resultant polymerization gives rise to the desired adhesive bond. When the monomeric form is too fluid at ordinary temperatures, it must be controlled in order to prevent undue escape of the adhesive from any given area to which the adhesive is applied. Additionally, sufficient time must be allowed for the monomeric material to polymerize and thus to bring about the desired bonding action.

It is generally known to add perfumes to α-cyanoacrylates adhesive compositions to control the smell of the compositions. See U.S. Pat. Nos. 4,171,416; 4,321,180; 4,582,648; 5,306,490; 5,480,935; 5,554,365; 5,665,817; 5,730,994; and 5,807,563, all of which disclose adding perfumes to adhesive compositions.

Additionally, U.S. Pat. No. 3,966,902 to Chromecek discloses that polymer complexes composed at least in part of a polymer containing hydrophilic functional groups or a precursor monomer and containing aluminum, zinc or zirconium metal bound in complex form can be prepared. See col. 1, lines 57–62. A portion of the monomer having complex forming groups can be replaced by a monomer that does not contain any complex forming group, such as cyanoacrylates. See col. 2, line 66-col. 3, line 5. The polymer complexes are then prepared by reacting the monomer with an aluminum salt prior to polymerization. See col. 3, line 66-col. 4, line 1. The polymer complexes may incorporate an antiperspirant, a pesticide, a medicine, or a fragrance. See col. 7, line 64- col. 8, line 2. Various formulations of the polymer complexes can incorporate a flavoring or sweetening agent such as natural anise flavor, a fragrance such as oil of orchids perfume essence and the like. See col. 7, line 64-col. 8, line 2. Specific examples of flavors also include peppermint, vanilla and rum. See Example 16. The formulations of complex polymers and an active agent can be applied to various surfaces including plastic, paper, glass, wood, skin and the like. See col. 8, lines 18–22.

Cyanoacrylate compositions for use in medical applications should often be sterile. However, not all medical applications require that the composition be sterile.

For example, it is not necessary for cyanoacrylate compositions for use in the mouth or for use on surface skin to be sterilized prior to application. However, when an additive is to be present in an α-cyanoacrylate composition and the composition is to be sterilized, the additive should be added prior to sterilization. In this manner, the additive can be sterilized as well, and the risk of the additive compromising the sterility is avoided.

Regardless of the type and number of additives, sterilization of α-cyanoacrylate adhesive compositions is often difficult to achieve. For example, widely practiced methods of sterilization, such as dry and moist heat sterilization, ionizing radiation, exposure to gas, and sterile filtration, are often not suitable for use with monomeric cyanoacrylate compositions. Problems arise due to polymerization of the monomer during the sterilization process. In many cases, sterilization-induced polymerization is so severe that the resulting product is unusable. Furthermore, sterilization is more difficult to achieve where other additives are included in the monomeric composition, particularly where the additives may themselves facilitate polymerization.

Methods currently used to package and sterilize α-cyanoacrylate monomer compositions have been developed with the recognition that, to improve efficiency and productivity, the packaging and sterilizing steps should be performed in rapid succession. However, these methods do not provide the desired viscosity of the adhesive compositions. For example, U.S. Pat. No. 5,530,037 to McDonnell et al. discloses that the composition of a sterilized adhesive would be very limited because necessary additives could not be conveniently added and mixed in a controlled fashion.

A need exists for flavored monomer cyanoacrylate adhesive compositions, for medical uses, without sacrificing the performance of the adhesive. The need also exists for a sterile, flavored monomeric adhesive composition that does not require pre-treatment of the flavoring additive prior to its combination with the monomeric adhesive.

SUMMARY OF THE INVENTION

The present invention provides flavored monomeric adhesive compositions comprising a monomer and a flavoring additive, including sterile compositions, and methods of making such compositions. Production of the flavored monomeric composition comprises mixing a flavoring additive with an adhesive-forming monomer such as a 1,1-disubstituted ethylene monomer. Production of the sterile, flavored composition includes placing a mixture of a polymerizable monomer and a flavoring additive in a container, sealing the container and sterilizing the container and the mixture. The flavoring additive is preferably soluble in the monomer at room temperature. A use of the flavored monomeric adhesive composition comprises applying the flavored monomeric adhesive composition to the inside of the mouth, and allowing the monomeric adhesive composition to polymerize.

DETAILED DESCRIPTION OF PREFERRED EMBODIMENTS

Figure 1:
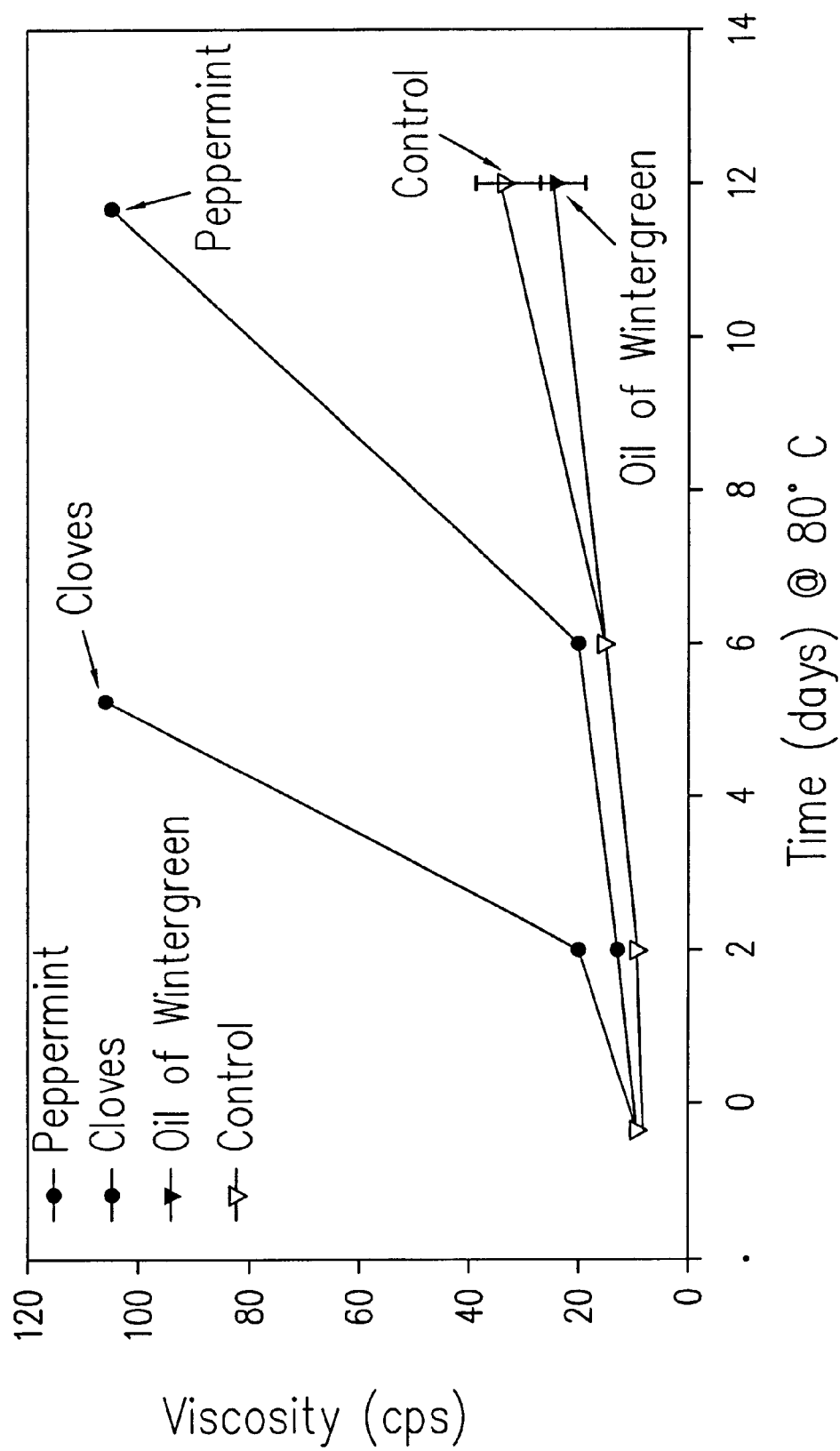
FIG. 1 is a graph showing viscosity stability results of stabilized 2-octyl cyanoacrylate monomer composition containing no flavorant or a selected flavorant in a simulated shelf-life test.

According to the invention, a flavored monomeric adhesive composition is manufactured by adding a flavoring additive to a composition comprising a monomer, preferably a polymerizable 1,1-disubstituted ethylene monomer.

A "flavoring additive" as used herein refers to any material that imparts flavor to or alters the flavor of a composition.

The flavoring additive may be selected, for example, from among fruit oil, vegetable oil, esters, heterocyclic compounds, fruit extract and vegetable extract. In particular, the flavoring additive may be selected from among any of the various known flavoring additives, including, but not limited to, 5-fold orange oil (Florida Chemical Co.), anethole (Aldrich), banana distillate (Florida Chemical Co.), benzaldehyde (Aldrich), clove oil (Humco), cold pressed valencia orange oil (Florida Chemical Co.), cold pressed grapefruit oil (Florida Chemical Co.), cold pressed lemon oil (Florida Chemical Co.), cold pressed lime oil (Florida Chemical Co.), cucumber distillate (Florida Chemical Co.), honey distillate (Florida Chemical Co.), menthol (Aldrich), alkyl salicylates such as methyl salicylate (Lorann Oils or Aldrich), monosodium glutamate, peppermint, peppermint oil (Humco), peppermint spirit, vanillin (Aldrich), thymol (Aldrich), and ethyl vanillin, mixtures thereof, and the like. In preferred embodiments, the flavoring additive is a flavoring agent as defined in 21 C.F.R. §172.510, dated Jun. 12, 1989, and §172.515, dated Apr. 1, 1996, the entirety of which is incorporated herein by reference. In other preferred embodiments, the flavoring additive includes, but is not limited to, 5-fold orange oil, anethole, benzaldehyde, clove oil, cold pressed valencia orange oil, cold pressed grapefruit oil, cold pressed lemon oil, cold pressed lime oil, menthol, methyl salicylate, peppermint oil, vanillin, and thymol, mixtures thereof, and the like.

The flavoring additive is selected such that it is compatible with the monomer (i.e., does not adversely affect polymerization, bond strength, cure properties, or shelf-life). Preferably, the flavoring additive is soluble in the monomer composition at room temperature (i.e., 20–25° C.) so that it may be added to the monomer composition without excessive heating or other solubilizing treatments of the monomer composition.

The flavoring additive is used in a flavoring effective amount, for example from about 0.001–25.0% by weight of the adhesive composition. In preferred embodiments, the flavoring additive is incorporated in an amount of from about 0.2–10.0%, more preferably 0.5–5.0%, of the adhesive composition. Of course, additive amounts outside of these ranges can be readily used depending upon, for example, the desired result to be achieved and the relative flavoring strength of the particular additive. The amount of flavoring additive to be used can be determined by one of ordinary skill in the art based on the present disclosure using known techniques without undue experimentation.

The flavored monomeric adhesive composition is produced by adding a flavoring additive to a polymerizable monomer composition, preferably a 1,1-disubstituted ethylene monomer composition. Once the flavored monomeric adhesive composition is produced, the composition may be applied to the desired surface or surfaces to be bonded, such as the inside of the mouth, including the tongue and/or gums, and allowed to polymerize. In embodiments, the composition may be applied to intact or compromised skin. Compromised skin may include, but is not limited to, skin that is cut, scraped or burnt. Intact skin may include, but is not limited to, skin that is healthy or uncut whether or not diseased, or infected by microorganisms.

In embodiments, the flavored adhesive composition has a viscosity of about 1–5000 centipoise, preferably 3–600 centipoise, more preferably 4–250 centipoise. The viscosity can be selected according to the proposed use—e.g., 4–50 centipoises for certain uses and 100–250 centipoises for other uses. Additionally, the composition may be a gel, e.g., 50,000–500,000 centipoise. A gel is a combination of a disperse phase with a continuous phase to produce a semi-solid material. The viscosity of the flavored adhesive composition is measured with a Brookfield Viscometer at 25° C. Additionally, in embodiments where a sterilization treatment is applied, the viscosity of the composition should preferably be maintained, or increased by a controlled and acceptable amount, after sterilization.

According to embodiments of the present invention, the stability, and thus the shelf-life, of some flavored monomeric adhesive compositions can be further enhanced and extended through careful regulation of the packaging (i.e., dispensing into a container) and/or any applied sterilizing procedure. In preferred embodiments, packaging and/or sterilization processes cause substantially no initiation of polymerization of monomeric liquid adhesive compositions that affects the utility of the monomer or monomers. Based on the present disclosure, one of ordinary skill in the art can readily test and select appropriate flavoring additives for a given monomer composition and sterilization conditions without undue experimentation. In particular, according to preferred embodiments, a polymerizable 1,1-disubstituted monomer and a flavoring additive are dispensed into a container. The container is then sealed and optionally subjected to sterilization without substantial polymerization of the monomer.

The flavored monomeric composition may be packaged in any type of suitable container fabricated from materials including, but not limited to, glass, plastic, metal packages, and film-formed packages. Suitable containers are those into which the compositions can be dispensed and optionally sterilized without unacceptable damage to, or degradation of, the container or the components of the monomer composition. Glass is preferred especially when sterilization is achieved with dry heat because of the lack of stability of many plastics at the temperatures used for dry heat sterilization (typically at least 160° C.). Examples of types of containers include, but are not limited to, ampoules, vials, syringes, pipettes, and the like. In a preferred embodiment, the container comprises a sealable container.

In embodiments, the flavored monomer compositions according to the invention are sterilized. The sterilization can be accomplished by techniques known to the skilled artisan, and is preferably accomplished by methods including, but not limited to, chemical, physical, and irradiation methods. Examples of chemical methods include, but are not limited to, exposure to ethylene oxide or hydrogen peroxide vapor. Examples of physical methods include, but are not limited to, sterilization by heat (dry or moist). Examples of irradiation methods include, but are not limited to, gamma irradiation, electron beam irradiation, and microwave irradiation. Preferred methods are dry and moist heat sterilization. Most preferred is dry heat sterilization. In embodiments where the compositions are to be used for medical applications, the sterilized composition must show low levels of toxicity to living tissue during its useable life.

The monomer composition is preferably a monomeric (including prepolymeric) adhesive composition. In embodiments, the monomer is a 1,1-disubstituted ethylene monomer, e.g., an α-cyanoacrylate. Preferred monomer compositions of the present invention, and polymers formed therefrom, are useful as tissue adhesives, sealants for preventing bleeding or for covering open wounds, and in other biomedical applications. They find uses in, for example, apposing surgically incised or traumatically lacerated tissues; retarding blood flow from wounds; drug delivery; dressing burns; dressing skin or oral tissues or other superficial or surface sores, ulcers, wounds or the like (such as abrasions, chaffed or raw skin, and/or stomatitis); and aiding repair and regrowth of living tissue. Other preferred monomer compositions of the present invention, and polymers formed therefrom, are useful in industrial and home applications, for example in bonding rubbers, plastics, wood, composites, fabrics, and other natural and synthetic materials.

Monomers that may be used in this invention are readily polymerizable, e.g. anionically polymerizable or free radical polymerizable, or polymerizable by zwitterions or ion pairs to form polymers. Such monomers include those that form polymers that may, but do not need to, biodegrade. Such monomers are disclosed in, for example, U.S. Pat. No. 5,328,687 to Leung, et al., which is hereby incorporated in its entirety by reference herein.

Useful 1,1-disubstituted ethylene monomers include, but are not limited to, monomers of the formula:

(I) $HRC=CXY$ wherein X and Y are each strong electron withdrawing groups, and R is H, $-CH=CH_2$ or, provided that X and Y are both cyano groups, a $C_1-C_4$ alkyl group.

Examples of monomers within the scope of formula (I) include α-cyanoacrylates, vinylidene cyanides, $C_1-C_4$ alkyl homologues of vinylidene cyanides, dialkyl methylene malonates, acylacrylonitriles, vinyl sulfinates and vinyl sulfonates of the formula $CH_2=CX'Y'$ wherein X' is $-SO_2R'$ or $-SO_3R'$ and Y' is $-CN$, $-COOR'$, $-COCH_3$, $-SO_2R'$ or $-SO_3R'$, and R' is H or hydrocarbyl.

Preferred monomers of formula (I) for use in this invention are α-cyanoacrylates. These monomers are known in the art and have the formula

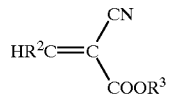

(II)

wherein $R^2$ is hydrogen and $R^3$ is a hydrocarbyl or substituted hydrocarbyl group; a group having the formula $-R^4-O-R^5-O-R^6$, wherein $R^4$ is a 1,2-alkylene group having 2–4 carbon atoms, $R^5$ is an alkylene group having 2–4 carbon atoms, and $R^6$ is an alkyl group having 1–6 carbon atoms; or a group having the formula

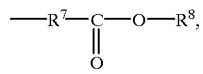

wherein $R^7$

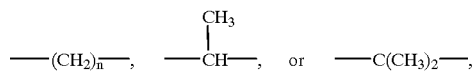

wherein n is 1–10, preferably 1–5 carbon atoms and $R^8$ is an organic moiety.

Examples of suitable hydrocarbyl and substituted hydrocarbyl groups include straight chain or branched chain alkyl groups having 1–16 carbon atoms; straight chain or branched chain $C_1-C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^8$ be substituted or unsubstituted and may be straight chain, branched or cyclic, saturated, unsaturated or aromatic. Examples of such organic moieties include $C_1-C_8$ alkyl moieties, $C_2-C_8$ alkenyl moieties, $C_2-C_8$ alknyl moieties, $C_3-C_{12}$ cycloaliphatic moieties, aryl moieties such as phenyl and substituted phenyl and aralkyl moieties such as benzyl, methylbenzyl, and phenylethyl. Other organic moieties include substituted hydrocarbon moieties, such as halo (e.g., chloro-, fluoro- and bromo-substituted hydrocarbons) and oxy-substituted hydrocarbon (e.g., alkoxy substituted hydrocarbons) moieties. Preferred organic radicals are alkyl, alkenyl, and alkynyl moieties having from 1 to about 8 carbon atoms, and halo-substituted derivatives thereof Particularly preferred are alkyl moieties of 4 to 6 carbon atoms.

In the cyanoacrylate monomer of formula (II), $R^3$ is preferably an alkyl group having 1–10 carbon atoms or a group having the formula $-AOR^9$, wherein A is a divalent straight or branched chain alkylene or oxyalkylene moiety having 2–8 carbon atoms, and $R^9$ is a straight or branched allyl moiety having 1–8 carbon atoms.

Examples of groups represented by the formula $-AOR^9$ include 1-methoxy-2-propyl, 2-butoxy ethyl, isopropoxy ethyl, 2-methoxy ethyl, and 2-ethoxy ethyl.

The α-cyanoacrylates of formula (II) can be prepared according to methods known in the art. U.S. Pat. Nos. 2,721,858 and 3,254,111, each of which is hereby incorporated in its entirety by reference, disclose methods for preparing α-cyanoacrylates. For example, the α-cyanoacrylates can be prepared by reacting an allyl cyanoacetate with formaldehyde in a non-aqueous organic solvent and in the presence of a basic catalyst, followed by pyrolysis of the anhydrous intermediate polymer in the presence of a polymerization inhibitor. The α-cyanoacrylate monomers prepared with low moisture content and essentially free of impurities are preferred for biomedical use.

The α-cyanoacrylates of formula (II) wherein $R^3$ is a group having the formula $R^4-O-R^5-O-R^6$ can be prepared according to the method disclosed in U.S. Pat. No. 4,364,876 to Kimura et al., which is hereby incorporated in its entirety by reference. In the Kimura et al. method, the α-cyanoacrylates are prepared by producing a cyanoacetate by esterifying cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The α-cyanoacrylates of formula (II) wherein $R^3$ is a group having the formula

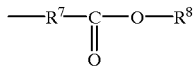

can be prepared according to the procedure described in U.S. Pat. No. 3,995,641 to Kronenthal et al., which is hereby incorporated in its entirety by reference. In the Kronenthal et al. method, such α-cyanoacrylate monomers are prepared by reacting an alkyl ester of an α-cyanoacrylic acid with a cyclic 1,3-diene to form a Diels-Alder adduct which is then subjected to alkaline hydrolysis followed by acidification to form the corresponding α-cyanoacrylic acid adduct The α-cyanoacrylic acid adduct is preferably esterified by an alkyl bromoacetate to yield the corresponding carbalkoxymethyl α-cyanoacrylate adduct. Alternatively, the α-cyanoacrylic acid adduct may be converted to the α-cyanoacrylyl halide adduct by reaction with thionyl chloride. The α-cyanoacrylyl halide adduct is then reacted with an alkyl hydroxyacetate or a methyl substituted alkyl hydroxyacetate to yield the corresponding carbalkoxymethyl α-cyanoacrylate adduct or carbalkoxy alkyl α-cyanoacrylate adduct, respectively. The cyclic 1,3-diene blocking group is finally removed and the carbalkoxy methyl α-cyanoacrylate adduct or the carbalkoxy alkyl α-cyanoacrylate adduct is converted into the corresponding carbalkoxy alkyl α-cyanoacrylate by heating the adduct in the presence of a slight deficit of maleic anhydride.

Examples of monomers of formula (II) include cyanopentadienoates and α-cyanoacrylates of the formula:

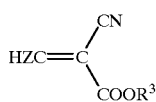

(III)

wherein Z is —CH=CH$_2$ and R$^3$ is as defined above. The monomers of formula (III) wherein R$^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated in its entirety by reference.

Preferred α-cyanoacrylate monomers used in this invention are alkyl α-cyanoacrylates including octyl cyanoacrylate, such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; methyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. More preferred monomers are n-butyl and 2-octyl α-cyanoacrylate. Monomers utilized for medical purposes in the present application should be very pure and contain few impurities (e.g., surgical grade). Monomers utilized for industrial purposes need not be as pure.

The composition may optionally also include at least one plasticizing agent that imparts flexibility to the polymer formed from the monomer. The plasticizing agent preferably contains little or no moisture and should not significantly affect the stability or polymerization of the monomer. Such plasticizers are useful in polymerized compositions to be used for closure or covering of wounds, incisions, abrasions, sores or other applications where flexibility of the adhesive is desirable. Some thickeners can also impart flexibility to the polymer e.g., poly-2-ethylhexylcyanoacrylate.

Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts ranging from about 0.5 wt. % to about 25 wt. %, or from about 1 wt. % to about 20 wt. %, or from about 3 wt. % to about 15 wt. % or from about 5 wt. % to about 7 wt. % provides increased elongation and toughness of the polymerized monomer over polymerized monomers not having plasticizing agents.

The composition may also optionally include at least one thixotropic agent. Suitable thixotropic agents are known to the skilled artisan and include, but are not limited to, silica gels such as those treated with a silyl isocyanate. Examples of suitable thixotropic agents are disclosed in, for example, U.S. Pat. No. 4,720,513, the disclosure of which is hereby incorporated in its entirety.

The composition may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The composition may also optionally include at least one stabilizing agent that inhibits polymerization. Such stabilizing agents may also include mixtures of anionic stabilizing agents and radical stabilizing agents. Any mixture of stabilizers is included as long as the mixture does not inhibit the desired polymerization of the monomer.

Examples of such suitable anionic stabilizing agents include, but are not limited to, sulfur dioxide, sulnfric acid, sulfonic acid, boron trifluoride, organic acids such as acetic acid, boron trifluoride, hydrogen fluoride, trifluoroacetic acid, picric acid, trichloroacetic acid, benzoic acid, and mixtures thereof. Preferably these anionic stabilizing agents are acidic stabilizing agents of organic acids such as acetic acid. In embodiments, the amount of acetic acid and/or benzoic acid is about 50–2000 ppm. Examples of suitable radical stabilizing agents include hydroquinone, hydroquinone monomethyl ether, catechol, pyrogallol, benzoquinone, 2-hydroxybenzoquinone, p-methoxy phenol, t-butyl catechol, butylated hydroxy anisole (BHA), butylated hydroxy toluene (BHT), t-butyl hydroquinone, and mixtures thereof. In embodiments, the amount of agents such as BHA is about 100–200,000 ppm, preferably 300–100,000 ppm, more preferably 500–20,000 ppm.

Suitable acidic stabilizing agents include those having aqueous pK$_a$ ionization constants ranging from −12 to 7, about −5 to about 7, preferably from about −3.5 to about 6. For example, suitable acidic stabilizing agents include: hydrogen sulfide (pK$_a$ 7.0), carbonic acid (pK$_a$ 6.4), triacetylmethane (pK$_a$ 5.9), acetic acid (pK$_a$ 4.8), benzoic acid (pK$_a$ 4.2), 2,4-dinitrophenol (pK$_a$ 4.0), formic acid (pK$_a$ 3.7), nitrous acid (pK$_a$ 3.3), hydrofluoric acid (pK$_a$ 3.2), chloroacetic acid (pK$_a$ 2.9), phosphoric acid (pa 2.2), dichloroacetic acid (pK$_a$ 1.3), trichloroacetic acid (pK$_a$ 0.7), 2,4,6-trinitrophenol (picric acid) (pK$_a$ 0.3), trifluoroacetic acid (pK$_a$ 0.2), sulfuric acid (pK$_a$ _3.0), sulfurous acid, and mixtures thereof.

When adding the above-mentioned acidic stabilizing agents to the adhesive composition, the addition of plasticizing agents in amounts ranging from about 0.5 wt. % to about 16 wt. %, preferably from about 3 wt. % to about 9 wt. %, and more preferably from about 5 wt. % to about 7 wt. % provides increased film strength (e.g., toughness) of the polymerized monomer over polymerized monomers having amounts of plasticizing agents and acidic stabilizing agents outside of the above ranges.

The concentration of the acidic stabilizing agents utilized may vary depending on the strength of the acid. For example, when using acetic acid, a concentration of 80–200 ppm (wt/wt), preferably 90–180 ppm (wt/wt), and more preferably 100–150 ppm (wt/wt) may be utilized. When using a stronger acid such as phosphoric acid, a concentration range of 20–80 ppm (wt/wt), preferably, 30–70 ppm (wt/wt) and more preferably 40–60 ppm (wt/wt) may be utilized. In embodiments, the amount of trifluoroacetic acid is about 100 to 3000 ppm, preferably 500–1500 ppm. In other embodiments, the amount of phosphoric acid is about 10–200 ppm, preferably about 50–150 ppm, and more preferably about 75–125 ppm.

Medical compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitrites; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium, and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic arnines such as, for example, aniline, benzidine, arninopynimidine, toluene-diamine, triethylenediarnine, diphenylamine, diaminodiphenylamine, hydrazines, and hydrazide.

Suitable proteins include collagen, gelatin, casein, soybean protein, vegetable protein, keratin, and glue. The preferred protein for use in this invention is casemn.

Suitable amides for use in this invention include urea, cyanamide, acrylamide, benzamide, and acetamide. Urea is a preferred amide.

Suitable alcohols include phenols, 1,4-butanediol, d-sorbitol, and polyvinyl alcohol.

Examples of suitable compounds having a b-dicarbonyl group include malonic acid, acetylacetone, ethylacetone, acetate, malonamide, diethylmalonate, or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 to Perry, which is hereby incorporated in its entirety by reference. Such heterocyclic compounds include, for example, benzinidazole, 5-methyl benzimidazole, 2-methylbenzimiidazole, indole, pyrrole, 1,2,4-triazole, indoline, benzotriazole, indoline, and the like.

A preferred formaldehyde scavenger for use in this invention is sodium bisulfite.

In practicing the present invention, the formaldehyde concentration reducing agent is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent may be used in this invention in either free form or in microencapsulated form. When microencapsulated, the formaldehyde concentration reducing agent is released from the microcapsule continuously over a period of time during the in vivo biodegradation of the cyanoacrylate polymer.

For purposes of this invention, the mnicroencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content. Such bioerosion can occur as a result of the physical or chemical breakdown of the encapsulating material, for example, by the encapsulating material passing from solid to solute in the presence of body fluids, or by biodegradation of the encapsulating material by agents present in the body.

Examples of coating materials that can be used to microencapsulate the formaldehyde concentration reducing agent include polyesters, such as polyglycolic acid, polylactic acid, poly-1,4-dioxa-2-one, polyoxalates, polycarbonates, copolymers of polyglycolic acid and polylactic acid, polycaprolactone, poly-b-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly (anhydrides); poly(alkyl-2-cyanoacrylates); poly (dihydropyrans); poly(acetals); poly(phosphazenes); poly (urethanes); poly(dioxinones); cellulose; and starches.

Examples of surfactants that can be added to the mineral oil include those commercially available under the designations Triton X-100™ (Rohm and Haas) (octoxynol), Tween 20™ (ICI Americas) (polysorbate), and Tween 80™ (ICI Americas) (polysorbate).

The composition of this invention may further contain one or more adjuvant substances, such as thickening agents, medicaments, or the like, to improve the medical utility of the monomer for particular medical applications.

Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate).

To improve the cohesive strength of adhesives formed from the compositions of this invention, difunctional monomeric cross-linking agents may be added to the monomer compositions of this invention. Such crosslining agents are known. U.S. Pat. No. 3,940,362 to Overhults, which is hereby incorporated in its entirety by reference, discloses such cross-linking agents. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator or rate modifier may be added to initiate polymerization or to modify the rate of polymerization of the cyanoacrylate monomer/crosslinking agent blend.

In embodiments, the adhesive compositions may additionally contain heat and/or light (e.g., visible or ultraviolet light) activated initiators and accelerators that initiate cross-linking of cyanoacrylate compositions containing compounds of formula (I).

Particular initiators for particular systems may be readily selected by one of ordinary skill in the art without undue experimentation. Suitable polymerization initiators for the cyanoacrylate compositions include, but are not limited to, detergent compositions; surfactants: e.g., nonionic surfactants such as polysorbate 20 (e.g., Tween 20™), polysorbate 80 (e.g., Tween 80™) and poloxamers, cationic surfactants such as tetrabutylammonium bromide, anionic surfactants such as benzalkonium chloride or its pure components, stannous octoate (tin (II) 2-ethylheaxanoate), and sodium tetradecyl sulfate, and amphoteric or zwitterionic surfactants such as dodecyldimethyl(3-sulfopropyl)ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; and organometallics and manganese acetylacetonate and radical initiators. Cobalt naphthenate can be used as an accelerator for peroxide.

The compositions of this invention may further contain fibrous reinforcement and colorants such as dyes, pigments, and pigment dyes. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl)axo]-2-naphthalene-sulfonic acid (FD+C Yellow No. 6); 9-(o-carboxyphen0yl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-IH-indole-5-sulfonic acid disodium salt (FD+C Blue No. 2); and [phthalocyaninato (2-)] copper.

Other compositions contemplated by the present invention are exemplified by U.S. Pat. Nos. 5,624,669; 5,582,834; 5,575,997; 5,514,371; 5,514,372; and 5,259,835; and U.S. Pat. Application Serial No. 081714,288, the disclosures of all of which are hereby incorporated in their entirety by reference.

The following examples illustrate specific embodiments of the present invention. One skilled in the art will recognize that the appropriate reagents, and component ratios/concentrations may be adjusted as necessary to achieve specific product characteristics. All parts and percentages are by weight unless otherwise indicated.

EXAMPLES

Examples 1–16

Various flavored 2-octyl cyanoacrylate monomer compositions are prepared by adding a selected amount of a flavorant to 2 mL of 2-octyl cyanoacrylate monomer. The mixture is then sealed in a glass vial and stirred. The characteristics of the compositions are recorded at about one minute after preparation and at twenty-four or more hours after preparation. Specific flavorants and the respective amounts added are identified in the following Table I. All solutions that are not indicated as "2 phase solutions" or "cloudy solution" are solutions in which the respective flavorant is soluble in the monomer.

TABLE I

| Example | Flavorant | Amount Added | Notes @ ~1 min | Notes @ 24+ Hours |
|---|---|---|---|---|
| 1 | 5-Fold Orange Oil | 100 uL | Dark Yellow Solution | Dark Yellow Solution |
| 2 | Anethole | 100 uL | Clear Solution | Clear Solution |
| 3 | Banana Distillate | 100 uL | 2 phase solution | Cloudy Solution |
| 4 | Benzaldehyde | 100 uL | Clear Solution | Clear Solution |
| 5 | Clove Oil | 400 uL | Clear Solution | Clear Solution |
| 6 | Cold Pressed Valencia Orange Oil | 100 uL | Yellow Solution | Yellow Solution |
| 7 | Cold Pressed Grapefruit Oil | 100 uL | Light Yellow Solution | Light Yellow Solution |
| 8 | Cold Pressed Lemon Oil | 100 uL | Light Yellow Solution | Clear Solution |
| 9 | Cold Pressed Lime Oil | 100 uL | Dark Yellow Solution | Yellow Solution |
| 10 | Cucumber Distillate | 100 uL | 2 phase solution | Cloudy Solution |
| 11 | Honey Distillate | 100 uL | 2 phase solution | Cloudy Solution |
| 12 | Menthol | 100 mg | Clear Solution | Clear Solution |
| 13 | Methyl Salicylate (Oil of Wintergreen) | 400 uL | Clear Solution | Clear Solution |
| 14 | Peppermint Oil | 400 uL | Clear Solution | Clear Solution |
| 15 | Thymol | 20 mg | Clear Solution | Clear Solution |
| 16 | Vanillin | 20 mg | Clear Solution | Clear Solution |

Example 17 and Comparative Example 1

Flavored compositions are prepared by adding 0.34% by weight of a flavorant to 2-octyl cyanoacrylate. This solution and a control are subjected to 80° C. in an oven for 0 and 12 days and tested for viscosities. This experiment is then repeated adding a 160° C. dry heat sterilization cycle first and then subjecting the solutions to 80° C. in an oven for 0 and 12 days, followed by testing for viscosities. Then, using the Arrhenius equation, 2 day data equal to a 4 month shelf life at 25° C., 6 day data equal to a 1 year shelf life at 25° C., and 12 day data equal to a 2 year shelf life at 25° C. are collected.

TABLE II

| | | Viscosity, cP* | | | |
|---|---|---|---|---|---|
| Example | Flavorant | 0 days | 0 days post 160° C. Dry Heat | 12 days @ 80° C. No Dry Heat | 12 days at 80° C. Post 160° C. Dry Heat |
| 17 | thymol | 6.2+/−0.1 | NA | 49.0+/−3.2 | NA |
| Comp 1 | none | 6.1+/−0.1 | NA | 21.0+/−10.0 | NA |
| 17 | thymol | 6.2+/−0.1 | 8.5+/−1.1 | NA | 209.0+/−7.6** |
| Comp 1 | none | 6.1+/−0.1 | 6.6+/−0.1 | NA | 20.4+/−1.8 |

*All results are the average of three readings.
**One sample was too thick to read.

Examples 18–20 and Comparative Example 2

Various flavored compositions are prepared by adding 2% by volume of three flavorants to 2-octyl cyanoacrylate. These solutions are then subjected to 80° C. in an oven for 0, 2, 6 and 12 days and tested for viscosities. Then, using the Arrhenius equation, 2 day data equal to a 4 month shelf life at 25° C., 6 day data equal to a 1 year shelf life at 25° C., and 12 day data equal to a 2 year shelf life at 25° C. are collected.

Both peppermint oil and clove oil require stabilizers to increase their shelf life to 2 years. Oil of wintergreen acts both as a flavorant and as a stabilizer at 2 years shelf life and could be used under current manufacturing conditions with little or no adjustments. The data is also presented graphically in FIG. 1, where the data points are averages of the respective samples.

TABLE III

| | | Flavor Stability | | | |
|---|---|---|---|---|---|
| Example | Flavorant | Viscosity T = 0 days @ 80° C. (cps) | Viscosity T = 2 days @ 80° C. (cps) | Viscosity T = 6 days @ 80° C. (cps) | Viscosity T =12 days @ 80° C. (cps) |
| 18 | Peppermint Oil | 7.0 | 10.7 | 19.4 | 100.0 |
| 19 | Clove Oil | 7.0 | 17.7 | 100.0 | 100.0 |
| 20 | Oil of wintergreen | 6.6 | 8.0 | 10.7 | 29.3 |
| Comp. 2 | Control | 6.6 | 8.1 | 9.9 | 39.0 |

Each data point is an average of 4 readings.

What is claimed is:

1. A monomeric adhesive composition comprising a polymerizable 1,1-disubstituted ethylene monomer and a flavoring additive, wherein said flavoring additive is contained in the composition in an amount of from about 5–25% by weight of the composition.

2. The composition of claim 1, wherein the 1,1-disubstituted ethylene monomer is an α-cyanoacrylate monomer.

3. The composition of claim 1, wherein said monomer is at least one member selected from the group consisting of n-butyl cyanoacrylate, 2-octyl cyanoacrylate, and ethyl cyanoacrylate.

4. The composition of claim 1, wherein the flavoring additive is selected from the group consisting of fruit oil, vegetable oil, esters, heterocyclic compounds, fruit extract and vegetable extract.

5. The composition of claim 1, wherein said flavoring additive is selected from the group consisting of 5-fold orange oil, anethole, banana distillate, benzaldehyde, clove oil, cold pressed valencia orange oil, cold pressed grapefruit oil, cold pressed lemon oil, cold pressed lime oil, cucumber distillate, honey distillate, menthol, alkyl salicylate, monosodium glutamate, peppermint oil, peppermint spirit, rose water, ethyl vanillin, thymol, vanillin and oil of wintergreen.

6. The composition of claim 1, wherein said flavoring additive is selected from the group consisting of 5-fold orange oil, anethole, benzaldehyde, clove oil, cold pressed valencia orange oil, cold pressed grapefruit oil, cold pressed lemon oil, cold pressed lime oil, menthol, methyl salicylate, peppermint oil, vanillin, and thymol.

7. The composition of claim 5, wherein said flavoring additive is oil of wintergreen.

8. The composition of claim 5, wherein said flavoring additive is peppermint oil or peppermint spirit.

9. The composition of claim 5, wherein said flavoring additive is thymol.

10. The composition of claim 1, wherein said flavoring additive is contained in the composition in an amount of from about 5–10.0% by weight of the composition.

11. The composition of claim 1, wherein the flavoring additive is soluble in said monomer at room temperature.

12. The composition of claim 1, wherein said composition has a viscosity of about 1–5000 centipoise at 25° C.

13. The composition of claim 1, wherein said composition has a viscosity of about 3–600 centipoise at 25° C.

14. The composition of claim 1, wherein said composition has a viscosity of about 4–50 or 100–250 centipoise at 25° C.

15. The composition of claim 1, wherein said composition is a gel.

16. The composition of claim 1, wherein said composition further comprises a stabilizing agent.

17. The composition of claim 1, wherein said composition further comprises a plurality of stabilizing agents.

18. The composition of claim 1, wherein said composition further comprises a plasticizing agent.

19. The composition of claim 1, wherein said composition is sterile.

20. A method of making a flavored monomeric adhesive composition, comprising mixing a flavoring additive with a polymerizable 1,1-disubstituted ethylene monomer, wherein said flavoring additive is contained in the composition in an amount of from about 5–25% by weight of the composition.

21. The method of claim 20, further comprising sterilizing said mixture.

22. A method of using the composition of claim 1, comprising:

applying the composition to oral tissue or intact or compromised skin, and allowing the composition to polymerize.

23. A method of making a sterile, flavored adhesive composition comprising:

placing a mixture of a polymerizable 1,1-disubstituted ethylene monomer and a flavoring additive in a container, sealing said container, and sterilizing the mixture in the container, wherein said flavoring additive is contained in the composition in an amount of from about 5–25% by weight of the composition.

24. The method of claim 23, wherein said sterilizing is performed by dry heat, gamma irradiation, electron beam irradiation, or microwave irradiation.

25. The method of claim 24, wherein said sterilizing is performed by dry heat.

26. The method of claim 24, wherein said sterilizing is performed by gamma irradiation.

27. The method of claim 24, wherein said sterilizing is performed by electron beam irradiation.

28. The method of claim 23, wherein said container is made from at least one material selected from the group consisting of glass, plastic, and metal.

29. The method of claim 28, wherein said container is made from plastic.

30. The method of claim 28, wherein said container is made from glass.

31. The method of claim 28, wherein said mixture fuirther comprises at least one stabilizer.

32. The monomeric adhesive composition of claim 1, wherein the flavoring additive is methyl salicylate.

33. The method of claim 20, wherein the flavoring additive is methyl salicylate.

34. The method of claim 23, wherein the flavoring additive is methyl salicylate.

35. The monomeric adhesive composition of claim 1, wherein the flavoring additive is menthol.

36. The method of claim 20, wherein the flavoring additive is menthol.

37. The method of claim 23, wherein the flavoring additive is menthol.

* * * * *